US006646263B2

(12) United States Patent
Kwakman et al.

(10) Patent No.: US 6,646,263 B2
(45) Date of Patent: Nov. 11, 2003

(54) METHOD OF X-RAY ANALYSIS IN A PARTICLE-OPTICAL APPARATUS

(75) Inventors: Laurens Franz Taemsz Kwakman, St. Ismier (FR); Kars Zege Troost, Eindhoven (NL)

(73) Assignee: FEI Company, Hillsboro, OR (US)

( * ) Notice: Subject to any disclaimer, the term of this patent is extended or adjusted under 35 U.S.C. 154(b) by 57 days.

(21) Appl. No.: 10/123,666

(22) Filed: Apr. 16, 2002

(65) Prior Publication Data

US 2002/0154731 A1 Oct. 24, 2002

(30) Foreign Application Priority Data

Apr. 19, 2001 (EP) .............................. 01401010

(51) Int. Cl.$^7$ .............................. G01N 23/00
(52) U.S. Cl. .......................... 250/310; 250/307; 378/46
(58) Field of Search ............................. 378/46; 250/310, 250/307, 305, 306

(56) References Cited

U.S. PATENT DOCUMENTS

| 5,656,811 A | * | 8/1997 | Itoh et al. ..................... 250/309 |
| 5,940,678 A | * | 8/1999 | Doong et al. .................. 438/14 |
| 5,990,478 A | * | 11/1999 | Liu .............................. 250/307 |
| 6,188,068 B1 | * | 2/2001 | Shaapur et al. ............. 250/307 |
| 6,194,720 B1 | * | 2/2001 | Li et al. ....................... 250/311 |
| 6,576,900 B2 | * | 6/2003 | Kelly et al. .................. 250/307 |

OTHER PUBLICATIONS

KL Pey and Alan J. Leslie "Focused Ion Beam Sample Preparation For High Spatial Resolution X–Ray Microanalysis" 1995 p. 40–48.

* cited by examiner

Primary Examiner—David V. Bruce
Assistant Examiner—Hoon Song
(74) Attorney, Agent, or Firm—Michael O. Scheinberg

(57) ABSTRACT

Samples such as semiconductor wafers may be subjected to an elementary analysis by irradiation by means of electrons and measurement of the X-rays 30 generated in the sample. In order to achieve a high spatial resolution, two adjacent holes 6, 8 are formed in the sample surface, leaving a very thin separating wall 10 between said holes and hence limiting the dimension of the interaction volume 24. However, electrons pass through the wall, thus generating disturbing X-rays in the walls of the hole 8 behind the wall. According to the invention the hole 8 behind the separating wall 10 is provided with a stopping material 12 of an elementary composition which deviates from that of the wall 10. If the wall to be analyzed contains silicon, the stopping material 12 should preferably be platinum or carbon.

7 Claims, 1 Drawing Sheet

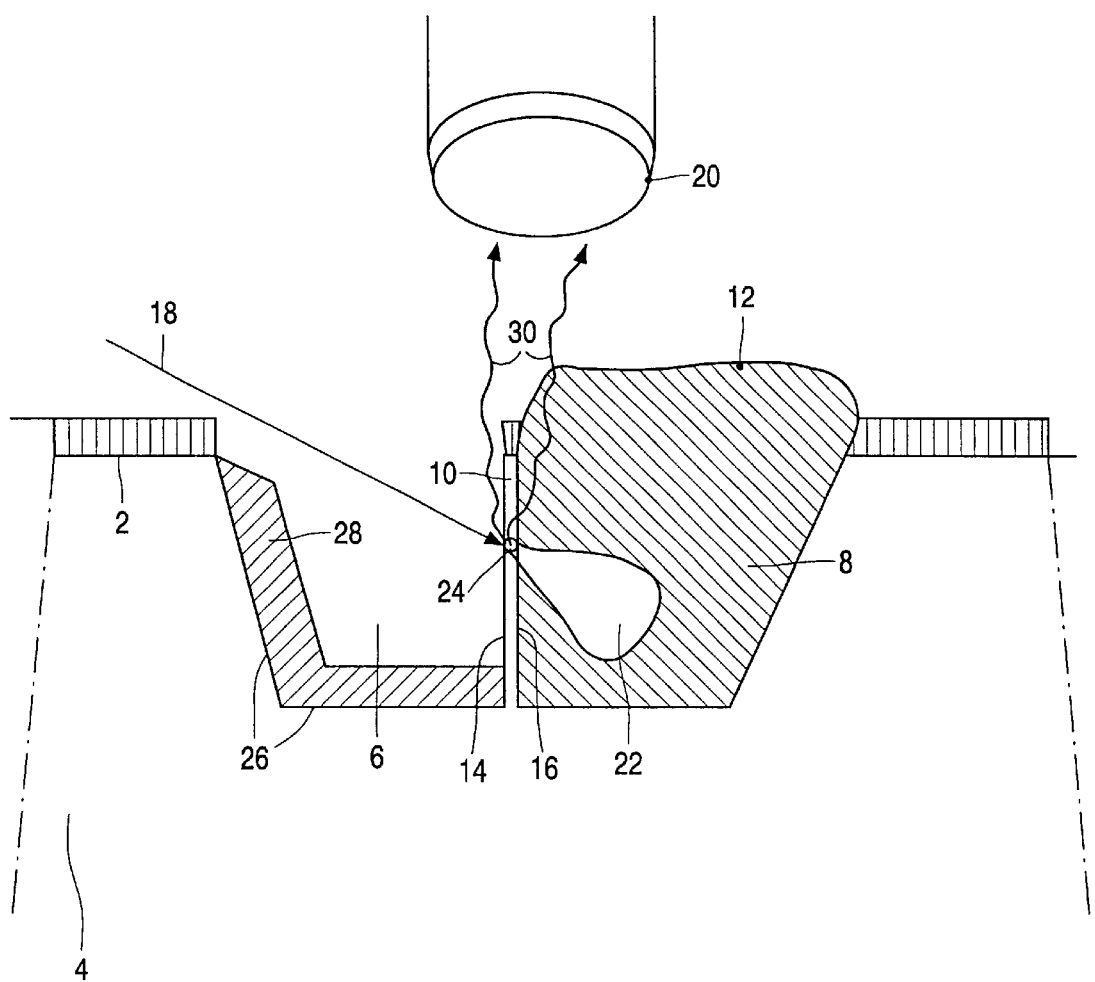

METHOD OF X-RAY ANALYSIS IN A PARTICLE-OPTICAL APPARATUS

The invention relates to a method for X-ray analysis of a sample in a particle-optical apparatus, in which:
a) two neighboring holes are formed in the sample, resulting in a separating wall between the holes,
b) a first side of the separating wall is irradiated by means of a beam of electrically charged particles, in response to which X-rays are generated in the separating wall, and
c) said X-rays are detected.

A method of this kind is known from a publication called "FOCUSED ION BEAM SAMPLE PREPARATION FOR HIGH SPATIAL RESOLUTION X-RAY MICROANALYSIS" in Proc. 1995 5th. int. symp. on the physical and failure analysis of integrated circuits (5th IPFA 1995 Singapore), pp. 40–48.

In order to determine the elementary composition of a material, a sample of the relevant material can be irradiated by means of charged particles of adequate energy (for example, electrons), in response to which the sample emits X-rays whose wavelength distribution is characteristic of the chemical elements occurring in the relevant material. Such a method can be used not only for determining the elementary composition of the material, but also for determining the variation of the concentration of a given element as a function of the depth in the specimen, or for the detection of defects in, for example, integrated circuits.

In order to achieve a favorable spatial resolution for said applications, a small cross-section may be imparted to the irradiating beam, so that only a limited zone is struck by the beam so as to emit X-rays. In that case it may be assumed that the X-rays detected originate from the zone of the sample on which the beam is incident. For particle beams having a cross-section of less than approximately a few micrometers, however, the dimensions of the zone emitting the X-rays are no longer determined exclusively by the beam cross-section, but to a substantial degree also by the scattering within the sample of particles incident on the sample. The scattering zone has approximately the shape of a pear whose longitudinal axis extends in the direction of incidence of the particle beam. The diameter of the scattering zone is then determined inter alia by the energy of the particles and amounts to from approximately 100 nm (for electrons of an energy of 2 keV) to 7000 nm (for electrons having an energy of 30 keV) in the case of a silicon sample. In this respect it is assumed that the cross-section of the beam is small in comparison with the scatter zone.

For analysis of samples it is also desirable to know the elementary composition of a sample at a given distance below the surface, that is, at a given depth in the sample. To this end, it is known to provide a pit-like recess in the sample, one of the walls of the pit or hole subsequently being exposed to the particle beam. However, upon such irradiation the spatial resolution is again limited by the scattering in the material of the sample.

In order to achieve a higher spatial resolution nevertheless, the cited publication proposes the formation of two neighboring pits or holes in the sample by means of a focused ion beam. This results in a separating wall of small thickness (order of magnitude of 100 nm) between the holes. A first side of the separating wall is then irradiated by an electron beam, in response to which X-rays are generated in the separating wall. Because of the small thickness of the separating wall, the electrons from the incident beam will hardly be scattered in the sample material but will pass more or less rectilinearly through the thin separating wall. The dimension of the scattering zone will then be approximately equal to the cross-section of the electron beam in the target plane.

It is a drawback of the known method that the electrons having traversed the thin separating wall lose only little energy while doing so and hence reach, via the hole on the other (non-irradiated) side of the separating wall, the sample material and generate disturbing X-rays therein as yet.

It is an object of the present invention to provide a method of the kind set forth in which the described disturbing of the X-ray analysis is counteracted. To this end, the method in accordance with the invention is characterized in that, prior to the irradiation of the separating wall, the hole situated to the other side of the separating wall is filled at least partly with a stopping material of a composition which deviates from that of the separating wall.

Because the composition of the stopping material deviates from that of the material to be analyzed, the X-rays generated therein will have a different spectral composition in comparison with the material to be analyzed, so that the X-rays emanating from the stopping material can be distinguished from the desired measuring signal. This is the case notably when the X-ray response of the stopping material is known. In that case it often suffices even to neglect the spectral lines of the stopping material in the overall detected spectrum, or to subtract the known spectrum of the stopping material from the overall spectrum.

In conformity with one version of the method in accordance with the invention the separating wall contains silicon and the stopping material is formed essentially by a solid element having an atomic number higher than 71. This version offers the advantage that such solid elements are mainly heavy metals in which the electrons having passed the separating wall travel only a small distance, and hence give rise to a small scattering zone only. As a result, X-rays originating from this zone, in as far as they still have a disturbing effect, will affect the spatial resolution to a minor degree only. Preferably, platinum is chosen as the stopping material from the above group, because it exhibits a weak chemical and/or physical interaction with the sample material and can be readily deposited.

In conformity with a further version of the method in accordance with the invention, the separating wall contains silicon and the stopping material is formed essentially by a solid element having an atomic number lower than 13. This version offers the advantage that said elements exhibit a comparatively low X-ray fluorescence and background radiation of low intensity. Moreover, a significant part of the radiation caused by such light elements is absorbed in optical elements in the optical path of the X-rays, for example, by the window of the X-ray detector. Preferably, carbon is chosen as the stopping material from the above group, because it exhibits a weak chemical and/or physical interaction with the sample material and can be readily deposited, for example by decomposition of a jet of organic gas (containing carbon) in an ion beam.

In another version yet of the method in accordance with the invention the walls of the hole situated to the first side of the separating wall are at least partly lined with a lining material of a composition which deviates from that of the separating wall. In given circumstances it may occur that incident electrons are reflected on the separating wall and subsequently penetrate the sample material surrounding the hole at the entrance side of the separating wall. When the locations in the hole where such reflected electrons are to be expected are lined with said material, the X-rays generated by the reflected electrons can be distinguished from the desired X-ray signal. Considering the previously mentioned advantages of carbon, notably carbon can be chosen as the lining material. Moreover, carbon does not reflect electrons, or only an insignificant amount of electrons, so that the electrons intercepted by the carbon do not make any further contribution in disturbing the desired X-ray signal.

The invention will be described in detail hereinafter with reference to the Figures. The sole FIGURE is a cross-sectional representation of a sample which is arranged so as to carry out the invention.

It is assumed that the sample to be analyzed has a flat upper side as in the case of a semiconductor wafer. The FIGURE shows a cross-section through the sample, that is, perpendicularly to the flat upper side 2, the bulk of the sample being denoted by the reference numeral 4.

During a first step of the method, two neighboring holes 6 and 8 are formed in the sample, that is, to both sides of the zone to be analyzed. The holes are situated near one another in such a manner that a separating wall 10 is formed between the two holes, said separating wall thus containing the zone 24 to be analyzed. The holes can be formed in a manner which is known per se, for example, by irradiating the sample by means of a focused ion beam (FIB) of suitably chosen ions such as gallium ions. Other ions such as aluminum ions or ions of heavy noble gases can also be used. During the formation of the holes there may be provided an electron stopping coating material so as to protect these parts of the surface (notably the top of the separating wall) against ions, if any, having escaped from the ion beam. The coating material may consist of platinum which is deposited in a known manner as will be described in detail hereinafter for the deposition of stopping material in one of the holes. It is also feasible to form the holes by irradiating the sample by means of a focused laser beam of short wavelength. The thickness of the separating wall 10 between the holes determines the spatial resolution of the method in accordance with the invention. This thickness is chosen in dependence on the desired X-ray resolution, for example, 10 nm.

After the formation of the holes in the sample to be examined, one of the holes, that is, the hole 8 adjoining the side 16 of the separating wall, is filled with a stopping material 12 which has an elementary composition which deviates from that of the separating wall 10. When the separating wall contains silicon, it is advantageous to choose a solid element having an atomic number higher than 71 for the stopping material, that is, preferably platinum in that case. Platinum offers the advantage that, because of its high atomic number (so its high atomic weight), this material has a high stopping power for the electrons passing the separating wall 10. In comparison with other elements having a high atomic number, platinum offers the advantage that it diffuses to a comparatively small degree only in the bulk of the sample and that it exhibits an X-ray spectrum that can be suitably distinguished from that of the elements to be determined, for example, silicon. A further stopping material may be formed by a solid element having an atomic number lower than 13, for example, boron, beryllium or carbon. Carbon offers the advantage that it has a low X-ray fluorescence and weak background radiation and that the X-ray spectrum generated therein is readily absorbed by the window material of an X-ray detector, thus mitigating the disturbing of the spectrum to be measured.

The deposition of the filling material 12 can take place in a manner which is known per se, for example, by means of IB-assisted CVD (Ion Beam-assisted Chemical Vapor Deposition). When a comparatively heavy element is to be deposited while utilizing this method, a CVD source gas, for example, platinum hexacarbonyl, containing the heavy element is introduced into the space above the hole 8 to be filled. This gas cloud is irradiated by a gallium ion beam at the area of the hole 8. As a result, the platinum is deposited in the hole 8 to be filled. If the desired stopping material is carbon, the hole 8 can be filled with a synthetic material, for example, an UV curing epoxy which is applied to the desired location by way of a micropipet. Such synthetic materials have a comparatively high carbon content.

After the hole 8 has been filled with the desired stopping material 12, the free side 14 of the separating wall 10 is irradiated by means of an electron beam 18. Because the method in accordance with the invention is preferably carried out in a scanning electron microscope (SEM), the electron source 18 originates from an electron source (not shown) which is customarily present in such an electron microscope. Preferably, the SEM is provided with a magnetic monopole electron lens, that is, a lens which is provided with one poleshoe only, the sample being situated directly underneath said poleshoe. Such lenses practically always have a funnel-like external appearance, so that a sample of comparatively large dimensions (for example, a semiconductor wafer having a diameter of 30 cm) can be tilted through a large angle (typically 60 degrees) relative to the optical axis. It is also possible to use an electrostatic electron lens, having a similar external appearance, in a SEM. The angle of incidence of the electron beam 18 can be varied over a large interval relative to the separating wall 10 by tilting the sample, so that it is practically always possible to make the beam incident on the separating wall at a desired angle. The electrons of the electron beam 18 generate X-rays 30 in the zone 24 to be analyzed, said X-rays being detected by an X-ray detector 20. This X-ray detector is preferably an Energy Dispersive X-ray detector (EDX detector) which offers the advantage that it can acquire a complete spectrum of the X-rays in one measurement, that is, the intensity of the detected radiation in dependence on the wavelength. The energy of the incident electron beam can be varied across a wide range, it being possible to take into account the nature of the material to be analyzed in the separating wall 10 as well as the electron stopping power of the stopping material 12. This energy may lie in the range of between 2 keV and 30 keV, the beam current being of the order of magnitude of some tens of pico-amperes. In conformity with the invention the wall thickness of the separating wall 10 is chosen to be such that the zone of interaction of the electrons and the material to be analyzed is small. This means that a significant part of the electrons passes through the separating wall 10 and is stopped in the stopping material 12. In the stopping material 12 there is thus formed a zone of interaction 22 in which X-rays are generated which, however, do not disturb the X-rays 30 to be detected, that is, the X-rays generated in the zone 24 to be analyzed.

A part of the electrons in the beam 18 is reflected by the material of the separating wall 10 and hence is quite likely to be incident on the material of the surrounding walls 26 of the hole 6, said wall usually having the same composition as the separating wall 10. Consequently, the wall 26 may also produce X-rays which, because of said same composition, cannot be distinguished from the X-rays emanating from the zone 24, so that such X-rays have a disturbing effect on the X-rays to be measured. In order to avoid the generating of such undesirable X-rays by reflected electrons, in accordance with the invention the walls 26 of the hole 6, that is, the hole situated at the entrance side 14 of the separating wall, are lined with a lining material 28 of a composition which deviates from that of the separating wall. When the separating wall contains silicon, the lining material 28 consists of a solid element having an atomic number lower than 13, for example, boron, beryllium or carbon, be it that preference is given to carbon. The advantage of an element having a low atomic number over an element having a comparatively high atomic number resides in the fact that an element such as, for example, carbon reflects electrons to a much lesser degree, so that the electrons originating from the side 14 are excluded, after interception by the lining material 28, from participation in further collision and reflection processes.

What is claimed is:

1. A method for X-ray analysis of a sample (4) in a particle optical apparatus, in which:
    a) two neighboring holes (6; 8) are formed in the sample (4), resulting in a separating wall (10) between the holes (6; 8),
    b) a first side (14) of the separating wall (10) is irradiated by means of a beam of electrically charged particles (18), in response to which X-rays (30) are generated in the separating wall, and
    c) said X-rays are detected,
characterized in that, prior to the irradiation of the separating wall (10), the hole (8) situated to the other side (16) of the separating wall is filled at least partly with a stopping material (12) of a composition which deviates from that of the separating wall.

2. A method as claimed in claim 1, in which the separating wall (10) contains silicon and the stopping material (12) is formed essentially by a solid element having an atomic number higher than 71.

3. A method as claimed in claim 2, in which the stopping material (12) is formed essentially by platinum.

4. A method as claimed in claim 1, in which the separating wall (10) contains silicon and the stopping material (12) is formed essentially by a solid element having an atomic number lower than 13.

5. A method as claimed in claim 4, in which the stopping material (12) consists mainly of carbon.

6. A method as claimed in claim 1, in which the walls (26) of the hole (6) situated to the first side (14) of the separating wall (10) are lined at least partly with a lining material (28) of a composition which deviates from that of the separating wall.

7. A method as claimed in claim 6, in which the separating wall contains silicon and the lining material (28) is formed essentially by a solid element having an atomic number lower than 13.

\* \* \* \* \*